(12) United States Patent
Loh

(10) Patent No.: US 12,303,240 B2
(45) Date of Patent: May 20, 2025

(54) NON-INVASIVE NON-COMPRESSIVE BLOOD PRESSURE MONITORING DEVICE

(71) Applicant: Jeffrey Thomas Loh, Honolulu, HI (US)

(72) Inventor: Jeffrey Thomas Loh, Honolulu, HI (US)

( * ) Notice: Subject to any disclaimer, the term of this patent is extended or adjusted under 35 U.S.C. 154(b) by 525 days.

(21) Appl. No.: 17/563,724

(22) Filed: Dec. 28, 2021

(65) Prior Publication Data

US 2022/0225885 A1 Jul. 21, 2022

Related U.S. Application Data

(60) Provisional application No. 63/248,647, filed on Sep. 27, 2021, provisional application No. 63/138,423, filed on Jan. 16, 2021.

(51) Int. Cl.
| | | |
|---|---|---|
| A61B 5/021 | (2006.01) | |
| A61B 5/00 | (2006.01) | |
| A61B 5/022 | (2006.01) | |
| A61B 5/024 | (2006.01) | |
| A61B 5/026 | (2006.01) | |
| A61B 5/0285 | (2006.01) | |

(Continued)

(52) U.S. Cl.
CPC ...... *A61B 5/02225* (2013.01); *A61B 5/02141* (2013.01); *A61B 5/024* (2013.01); *A61B 5/0261* (2013.01); *A61B 5/0285* (2013.01); *A61B 5/681* (2013.01); *A61B 2560/0223* (2013.01)

(58) Field of Classification Search
CPC ..... A61B 5/0225; A61B 5/0214; A61B 5/024; A61B 5/0261; A61B 5/0285; A61B 5/681; A61B 5/02108; A61B 5/02116; A61B 5/02438; A61B 5/0244; A61B 5/332; A61B 2560/0223
See application file for complete search history.

(56) References Cited

U.S. PATENT DOCUMENTS

| | | |
|---|---|---|
| 5,241,964 A | 9/1993 | McQuilkin |
| 6,589,186 B2 | 7/2003 | Nishibayashi |
| 10,052,036 B2 | 8/2018 | Lading et al. |

(Continued)

FOREIGN PATENT DOCUMENTS

| | | |
|---|---|---|
| DE | 3345739 C2 | 10/1986 |
| EP | 2437654 B1 | 10/2014 |

(Continued)

OTHER PUBLICATIONS

PCT/US21/73137 Application International Preliminary Report on Patentability, mailed Jul. 4, 2023.

(Continued)

*Primary Examiner* — Boniface N Nganga
(74) *Attorney, Agent, or Firm* — Batt IP A Law Corporation; Richard Batt

(57) ABSTRACT

A blood pressure monitoring device includes a wrist strap, a case, and a display. The strap portion is adapted to fasten the device to the wrist without occluding blood flow. At least one doppler probe is arranged within the case for obtaining doppler signals from an artery in the wrist. A processor within the case is operable to compute mean arterial pressure, and optionally diastolic and systolic blood pressure based on the doppler signals. Related methods are also described.

21 Claims, 9 Drawing Sheets

(51) Int. Cl.
  *A61B 8/04* (2006.01)
  *A61B 8/06* (2006.01)

(56) References Cited

U.S. PATENT DOCUMENTS

| | | |
|---|---|---|
| 10,722,131 B2 | 7/2020 | Banet et al. |
| 2002/0055680 A1 | 5/2002 | Miele et al. |
| 2008/0001735 A1 | 1/2008 | Tran |
| 2015/0327784 A1 | 11/2015 | Lading et al. |
| 2016/0228010 A1 | 8/2016 | Kim et al. |
| 2017/0231578 A1* | 8/2017 | Lading ............... A61B 5/0261 600/473 |
| 2018/0078155 A1 | 3/2018 | Baek et al. |
| 2019/0150749 A1 | 5/2019 | Harris et al. |
| 2019/0269914 A1 | 9/2019 | Moaddeb et al. |
| 2020/0305730 A1 | 10/2020 | Denney, Jr. et al. |

FOREIGN PATENT DOCUMENTS

| | | |
|---|---|---|
| WO | 2019160877 A1 | 8/2019 |
| WO | 2019223796 A1 | 11/2019 |

OTHER PUBLICATIONS

Stalmans et al., Acta Ophthalmol. 2011: 89: e609-e630.
Wang et al, Ultrasound-mediated biophotonic imaging Disease Markers, 19 (2003, 2004) 123 to 138.
PCT/US2021/073137 ISRWO, dated Mar. 17, 2022.
Jonas Adler et al, "Solving ill-posed inverse problems using iterative deep neural networks", Inverse Problems, vol. 33, Issue 12, (2017).
Stalmans et al., Acta Ophthalmologica 2011.
Wang, Disease Markers 19 (2003,2004) 123-138.

* cited by examiner

NON-INVASIVE NON-COMPRESSIVE BLOOD PRESSURE MONITORING DEVICE

CROSS-REFERENCE TO RELATED APPLICATIONS

This application claims priority to provisional application No. 63/138,423, filed Jan. 16, 2021, and entitled "NON-INVASIVE NON-COMPRESSIVE BLOOD PRESSURE MONITORING DEVICE", and provisional application No. 63/248,647, filed Sep. 27, 2021, and entitled "NON-INVASIVE NON-COMPRESSIVE BLOOD PRESSURE MONITORING DEVICE", each of which is incorporated by reference in its entirety for all purposes.

BACKGROUND OF THE INVENTION

The invention relates to blood pressure measurement, and more particularly, to non-invasively non-compressive measurement of mean arterial pressure based on doppler signals.

Mean arterial pressure (MAP) is the average blood pressure in an individual during a single cardiac cycle. MAP is considered to be the perfusion pressure seen by organs in the body. If the MAP is low for a substantial time, the vital organs will not get enough oxygen.

MAP can be measured directly by invasive monitoring. Additionally, at normal resting heart rates, MAP can be approximated by measuring the systolic blood pressure (SBP) and diastolic blood pressure (DBP) and applying a formula in which the lower (diastolic) blood pressure is doubled and added to the higher (systolic) blood pressure and that composite sum then is divided by 3, or.

$$MAP \approx (2 \times DBP + SBP)/3 \quad [1]$$

The SBP and DBP can be measured with traditional blood pressure cuff devices. However, such devices are undesirable because the blood vessels are occluded. Additionally, due to the occluding nature of these types of devices, they are not wearable for any extended period of time. Thus, cuff-based devices do not serve well for continuous blood pressure monitoring.

There have been attempts to make a cuffless blood pressure device including, for example, the use of pulse transit time (PTT). However, PTT is not convenient nor reliable because PTT requires taking data at multiple points on the body.

Examples of other types of cuffless blood pressure devices measure elevational changes or vessel distention. See, for example, U.S. Pat. No. 10,052,036 and International Patent Publication No. WO 2019/223796. However, in view of the small amount of skin distension arising from the change in blood vessel diameter, accurate measurement is challenging. Firm placement and location of the device also would appear challenging in order to obtain the distention or air pressure data arising from the skin distension.

Notwithstanding the above, an apparatus and method that overcomes the above mentioned challenges is still desirable.

SUMMARY OF THE INVENTION

A blood pressure monitoring device for computing mean arterial pressure of a user includes a case and a strap adapted to hold the case against the wrist of the patient. At least one doppler probe is arranged within the case and aimed at an artery in the wrist when the case is strapped to the wrist. A processor is arranged within the case and operable to: compute a plurality of features from the velocity data generated by the doppler probe; and compute the mean arterial pressure (MAP) based on the plurality of features.

In embodiments, a method for monitoring mean arterial pressure (MAP) of a person comprises: activating at least one doppler probe aimed at an artery in the wrist of the person to generate doppler velocity data; and automatically computing on a processor: a plurality of features from the doppler velocity data; and the MAP of the user based on the plurality of features.

Optionally, SBP and DBP are computed based on the plurality of features.

In embodiments, a display on the case presents the blood pressure information to the user.

In embodiments, a blood pressure monitoring system for computing mean arterial pressure of a user comprises: a case and a window adapted to be held against the skin of the patient; at least one doppler probe arranged within the case; and a processor. The processor is arranged and operable to: compute a plurality of features from velocity data arising from one or more of the doppler probes; and to compute the mean arterial pressure (MAP) based on the plurality of features.

In embodiments, the case further comprises a light emitter to direct light through the window towards the artery. The doppler velocity data is based, at least in part, on the absorption of the light by the artery and blood flow therethrough.

In embodiments, the plurality of features comprise viscosity, heart rate, and radius of the artery.

In embodiments, the processor is further operable to compute diastolic blood pressure (DBP) based on the velocity data, and optionally, to compute systolic blood pressure based on the computed MAP and DBP.

In embodiments, the blood pressure monitoring system comprises a trained model for determining MAP based on the plurality of features extracted from the velocity data.

In embodiments, the blood pressure monitoring system further comprises a console, and the processor is enclosed within the console. The case, window, light emitter, and at least one doppler probe can be incorporated together as a handheld tool connected to the console by an umbilical cord.

In embodiments, the blood pressure monitoring system comprises a plurality of doppler probes, at least one of which sends acoustic waves towards the artery and at least one doppler probe receives acoustic waves from the artery.

In embodiments, at least one doppler probe serves to receive acoustic waves generated by the light and optionally, acoustic waves generated by another doppler probe.

In embodiments, the processor is operable to alert the user an optimal location at which to hold or secure the case to the skin. In embodiments, and when the location mode is activated, the apparatus provides visual or audio alerts to the user in the form of light or sound changes corresponding to changes in the velocity as the apparatus is moved along the skin of the user.

In embodiments, the processor is operable to prompt the user for an actual blood pressure-related reading, and to compute a patient-specific proportionality factor based on the actual blood pressure-related reading, and wherein the MAP is based on the patient-specific proportionality factor.

Advantages of Embodiments of the Present Invention

Embodiments of the present invention are capable of determining the pressure values without measurement of elevation, or elevation changes.

Embodiments of the present invention are capable of determining the pressure values without measurement of distention, or distension changes.

Embodiments of the present invention are capable of determining the pressure values without measurement of air pressure, or air pressure changes.

Embodiments of the present invention are capable of determining the pressure values without measuring information at multiple anatomical areas.

Embodiments of the present invention are capable of determining the pressure values based on the doppler velocity data arising from a non-invasive wearable bracelet-like device.

Still other descriptions, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Overview

Figure 1:
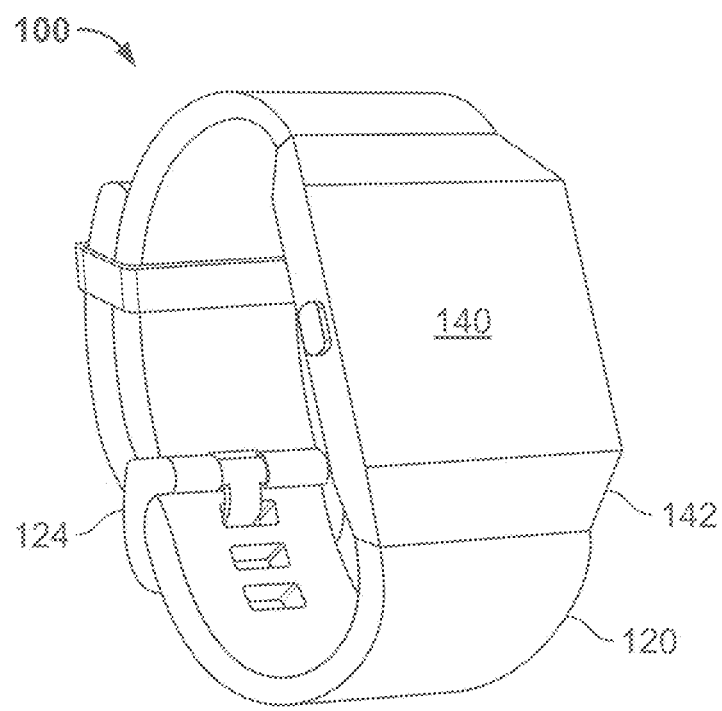
FIG. 1 is front side perspective view of a blood pressure monitoring device in accordance with one embodiment of the invention.

FIG. 1 illustrates a blood pressure monitoring device 100 in accordance with an embodiment of the invention. The blood pressure monitoring device 100 is shown having a strap 120, buckle 124, and a display 140 arranged on a case 142. The strap and case are sized and operable to be snugly fastened to the human wrist (not shown) and without compressing, occluding, distending, or otherwise interfering with the user's vasculature.

Figure 2:
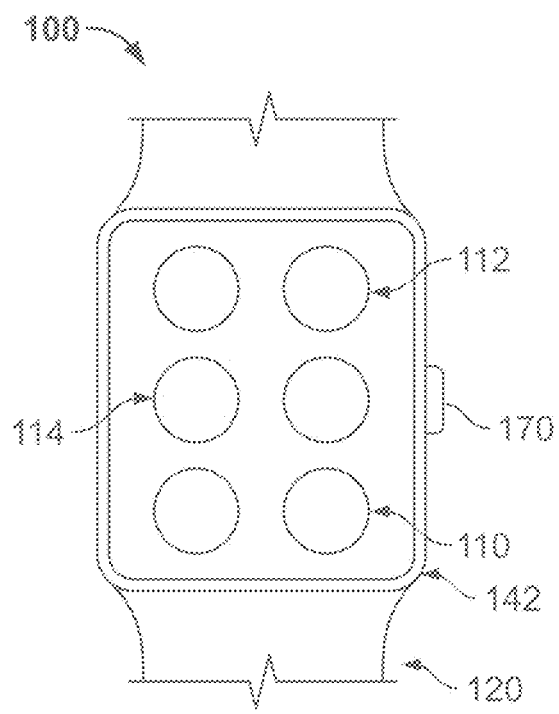
FIG. 2 is an enlarged rear view of a portion of the blood pressure monitoring device shown in FIG. 1.

With reference to FIG. 2, the backside of the case 142 shows a plurality of pairs of doppler probes 110, 112, 114 for obtaining blood flow information from which blood pressure values are automatically computed, discussed further herein. In embodiments, a thin window or protective layer is disposed over the sensors on the backside of the case. The window can be made of material that permits acoustic and optionally electromagnetic waves to pass therethrough.

Figure 3:
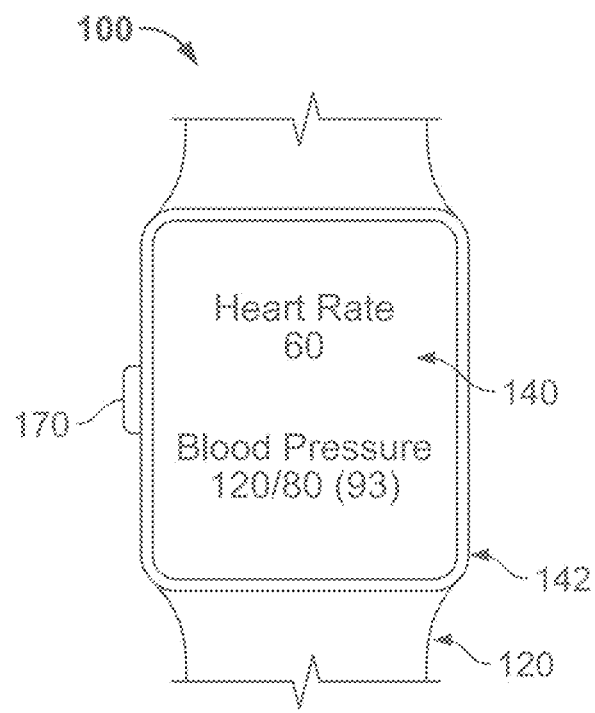
FIG. 3 is an enlarged front view of a portion of the blood pressure monitoring device shown in FIG. 1.

With reference to FIG. 3, the display 140 is operable to show various blood pressure information including, without limitation, heart rate (HR), systolic blood pressure (SBP), diastolic blood pressure (DBP), mean arterial pressure (MAP), and optionally date and time. Optionally, one or more buttons 170 are located on the case for controlling the device to carry out various functions such as for, example, calibration mode, location mode, and/or monitoring mode, discussed further herein.

Figure 4:
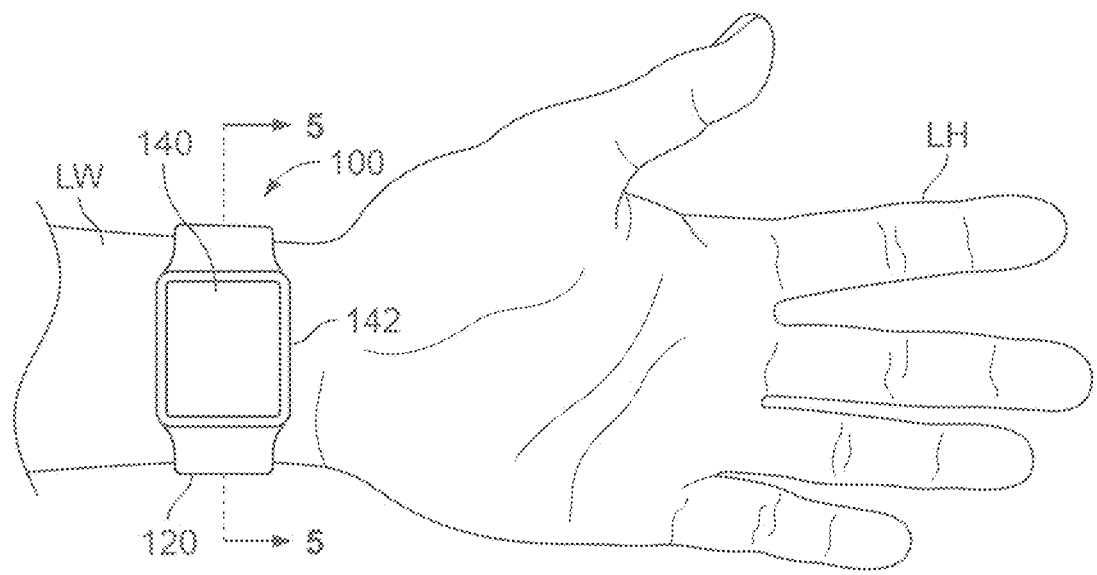
FIG. 4 shows a front view of a blood pressure monitoring device placed on the left wrist in accordance with an embodiment of the invention.

FIG. 4 shows a blood pressure monitoring device 100 fastened to the left wrist (LW) of a user in accordance with an embodiment of the invention. The rear side of the case lies flat against the inside of the left wrist when fastened.

In embodiments, the device comprises a location mode or module that is operable to select which sensor or sensor pair shall be used for the blood pressure monitoring mode. In embodiments, the device is programmed to automatically evaluate which sensor or sensor combination is best based on which sensor or sensor combination shows the greatest signal/doppler pickup. Optionally, (e.g., if signal perception is less than sufficient), the device will prompt the user to move the location of the device along the user's skin until an optimal signal is detected, discussed further herein. The location mode can thus provide an optimum sensor combination for each location, as well as an optimum location in view of each of the sensor combinations available for the device.

Additionally, in embodiments, during the blood pressure monitoring mode, the device is operable to automatically periodically check each of the sensors for signal strength, and to select the sensor combination with the greatest signal. This step serves to continuously ensure that the optimal sensors are used for blood pressure monitoring.

Figure 5A:
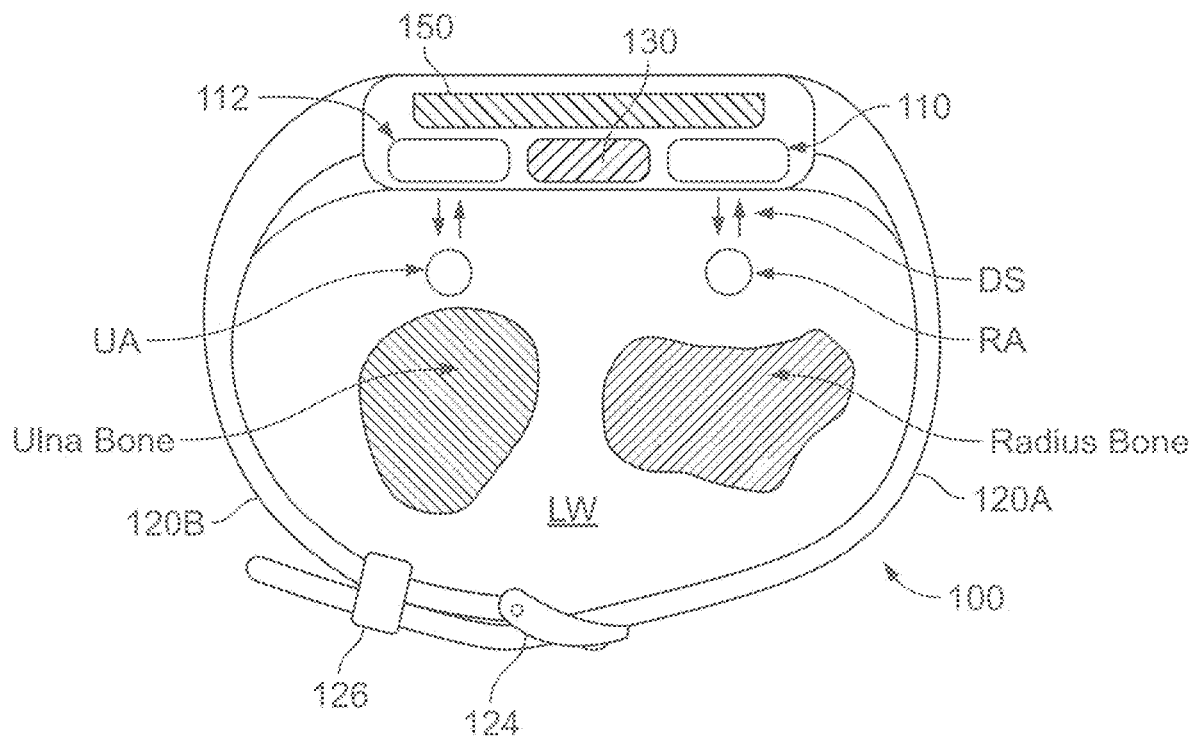
FIG. 5A is a cross sectional view of the illustration shown in FIG. 4 taken along line 5-5.

FIG. 5A is an enlarged cross sectional view of the illustration shown in FIG. 4 taken along line 5-5. The doppler probes 110, 112 are located above the radial artery (RA) and ulnar artery (UA) respectively. Doppler signals (DS) are shown being directed and reflected between the doppler probes and arteries. Also shown in FIG. 5A is rechargeable battery 130, processor board/CPU 150, and electronics operable to control and evaluate the doppler signals as well as control the display and other user functionality as described further herein.

Figure 5B:
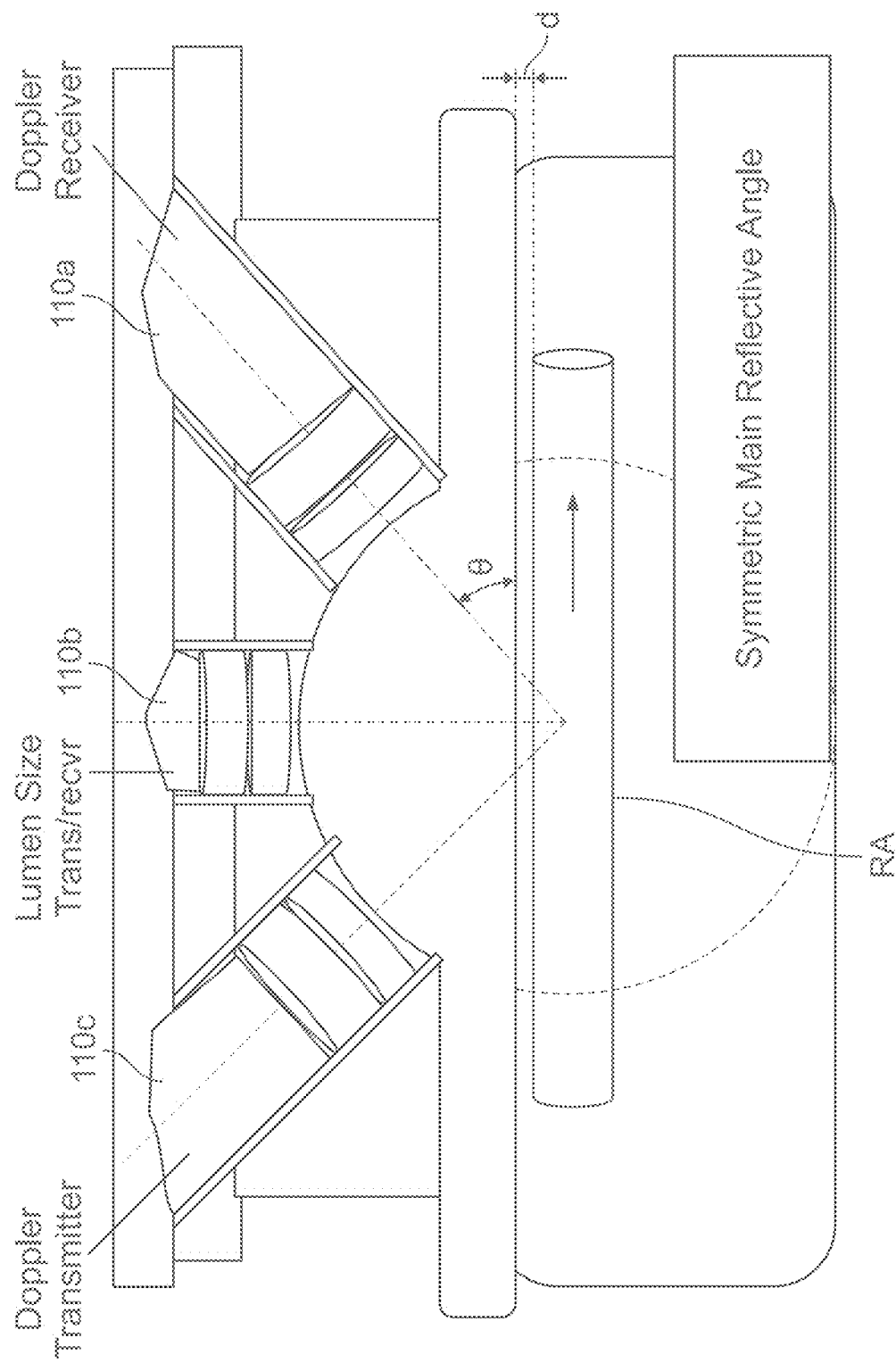
FIG. 5B is an illustration of an alternative arrangement of the doppler probes in accordance with an embodiment of the invention.

FIG. 5B is an illustration of an alternative arrangement of the doppler probes 110a, 110b, 110c aimed at vessel (RA) in accordance with an embodiment of the invention. The vessel (RA) is shown a distance (d) from the skin which typically ranges from 2-5 mm. Particularly, doppler receiver 110a and transmitter 110c are shown symmetrically disposed about doppler probe 110b defined by an angle (theta) from the vessel (RA). Doppler probe 110b is configured to both transmit and receive sound whereas probe 110a is dedicated to receive sound waves and probe 110c is dedicated to transmit sound waves. The three probes are also shown axially spaced along the vessel (RA). The symmetric main reflective angle (theta) is shown as about 45 degrees, however, in other embodiments, the angle (theta) is more or less than 45 degrees. An exemplary range for angle (theta) is 30-60 degrees, and more preferably 40-50 degrees.

In embodiments, the multiple probes are arranged in the case 142 such that the vertex of the symmetric main reflective angle (theta) is located within the vessel (RA) and more preferably, the multiple probes are arranged in the case 142 such that the vertex of the symmetric main reflective angle (theta) is located on the centerline of the vessel (RA), which in some embodiments is about 4-8 mm from the skin.

The PZT elements may be pulsed or continuous at 1 MHZ, for example. Additionally, the size of the PZT elements may vary. In one embodiment, for example, the PZT element has a diameter of about 4-6 mm, and a thickness of about 1 mm.

System Architecture

Figure 6:
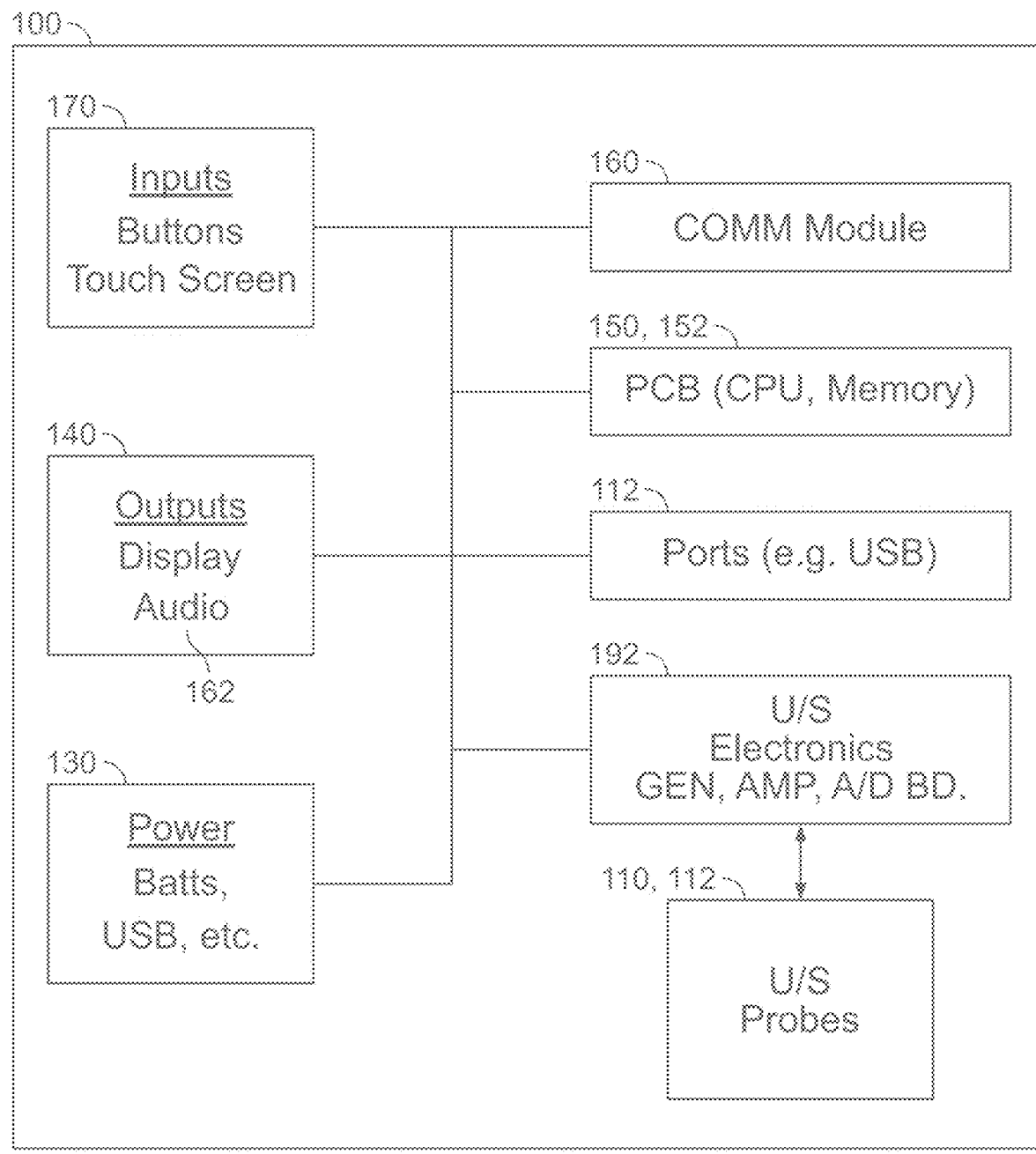
FIG. 6 is a block diagram of the blood pressure monitoring device in accordance with one embodiment of the invention.

FIG. 6 is a block diagram of a blood pressure monitoring device 100 in accordance with an embodiment of the invention. The device includes a plurality of doppler probes 110, 112, ultrasound electronics 192, and a main printed circuit board supporting a CPU 150. As discussed further herein, the CPU and ultrasound electronics are operable to control the doppler probes and to evaluate the audio doppler signals arising from the doppler probes. Although at least one doppler probe is required, more preferably there are 2-10 doppler probes arranged in the case such that when the device is fastened to the wrist of the user several of the doppler probes are in close proximity to the arteries to be interrogated. In embodiments, the case holds 2-6 doppler probes arranged as shown in FIG. 2.

FIG. 6 also shows battery (preferably rechargeable battery) 130, display 140, memory 152, communication interface 160 (preferably a wireless near field communication module such as Bluetooth®), USB (or another type of charging and data transfer port) 112, and button 170 in communication with one another.

The memory 152 stores data, information, and computer programs containing instructions for the CPU or other components of the blood pressure monitoring device 100. The types of information stored may vary and include, without limitation, raw data of doppler signals, processed doppler signals, extracted features, patient personal information, vitals, SVP, DBP, HR, MAP.

Optionally, in embodiments, the information is transmitted to remote devices (e.g., remote server, local server or computer, cloud, etc.) for safekeeping or otherwise.

Additionally, in embodiments, the device is operable to alert the user based on evaluating the information. If information is outside a predetermined range, the device alerts the user. Examples of alerts include an audible alarm via audio component 162, a visual graphic indicated on the display 140, a text or email sent to the user or hospital care, etc. Examples of types of information which would generate an alert if outside the predetermined range include, without limitation, battery or power source level, vital value, MAP, SBP, or DBP values, etc.

Doppler Probe

Figure 7:
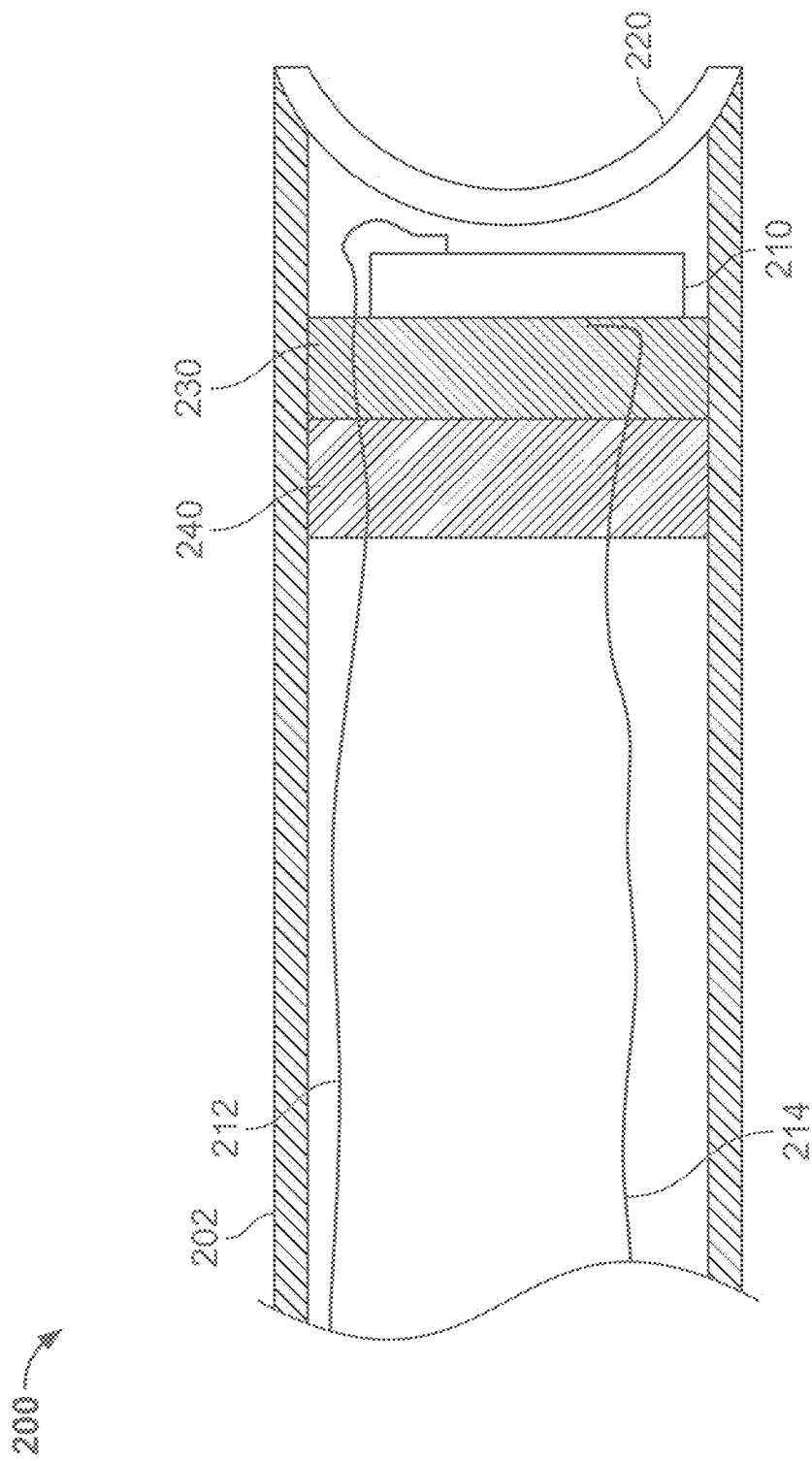
FIG. 7 is an enlarged cross sectional view of a doppler probe in accordance with an embodiment of the invention.

An example of a portion of a doppler probe in accordance with the present invention is shown in FIG. 7. The probe 200 is shown having a piezoelectric material 210 mounted at the end of a tube 202. Wire leads 212, 214 are shown joined to the front and back surfaces, respectively, of the piezoelectric material 210. A flexible insulating foam 230 is arranged on the back of the piezoelectric element. An epoxy 240 sets the components in place. In embodiments, the piezoelectric material consist of an approximately 1 mm square of 10- or 20-MHz piezoelectric material mounted at the end of a 2-mm-diameter, 3-10 mm-long stainless steel tube. A concave epoxy lens 220 is molded to the front face of the piezoelectric element to focus the sound beam at a depth of 4-10 mm under the skin, and in some embodiments at least 7 mm under the skin. The probe is preferably configured with the case to direct doppler energy at the skin. In embodiments, the doppler probe directs a signal at an angle of less than or equal to 45 degrees from the parallel to the skin. An example of a doppler probe which may be used in accordance with the invention is a non-imaging ultrasound pencil probe such as the Philips D5cwc Doppler Probe manufactured by Koninklijke Philips N. V. (Eindhoven, The Netherlands)(hereinafter referred to as "Philips").

As discussed above, the doppler probes 110, 112, 114 operate with ultrasound electronics 192. The ultrasound electronics can include a circuit portion for driving the sensors and preprocessing the signals from the sensors prior to sending them to the central processor 150. The circuit portion can include wave generating and amplifying components to drive the sensors. The circuit portion can also include amplifying and filtering components for the incoming electrical signals from the sensors as well as a microcontroller which receives the filtered and amplified signals, converts them to digital output signals, and sends them to the CPU 150, or elsewhere. An example of an ultrasound electronic console which is operable with a wide variety of doppler probes is the EPIQ 7 Ultrasound Machine, also manufactured by Philips.

Mean Arterial Pressure Model/Derivation

As described above, embodiments of the invention compute mean arterial pressure (MAP). MAP is defined according to the following equation:

$$MAP = \text{Cardiac Output } (CO) \times \text{Systemic Vascular Resistance } (SVR), \quad [2]$$

where the cardiac output (CO) is equal to the heart rate (HR) multiplied by the stroke volume (SV), or $$CO = HR \times SV. \quad [3]$$

Figure 9:
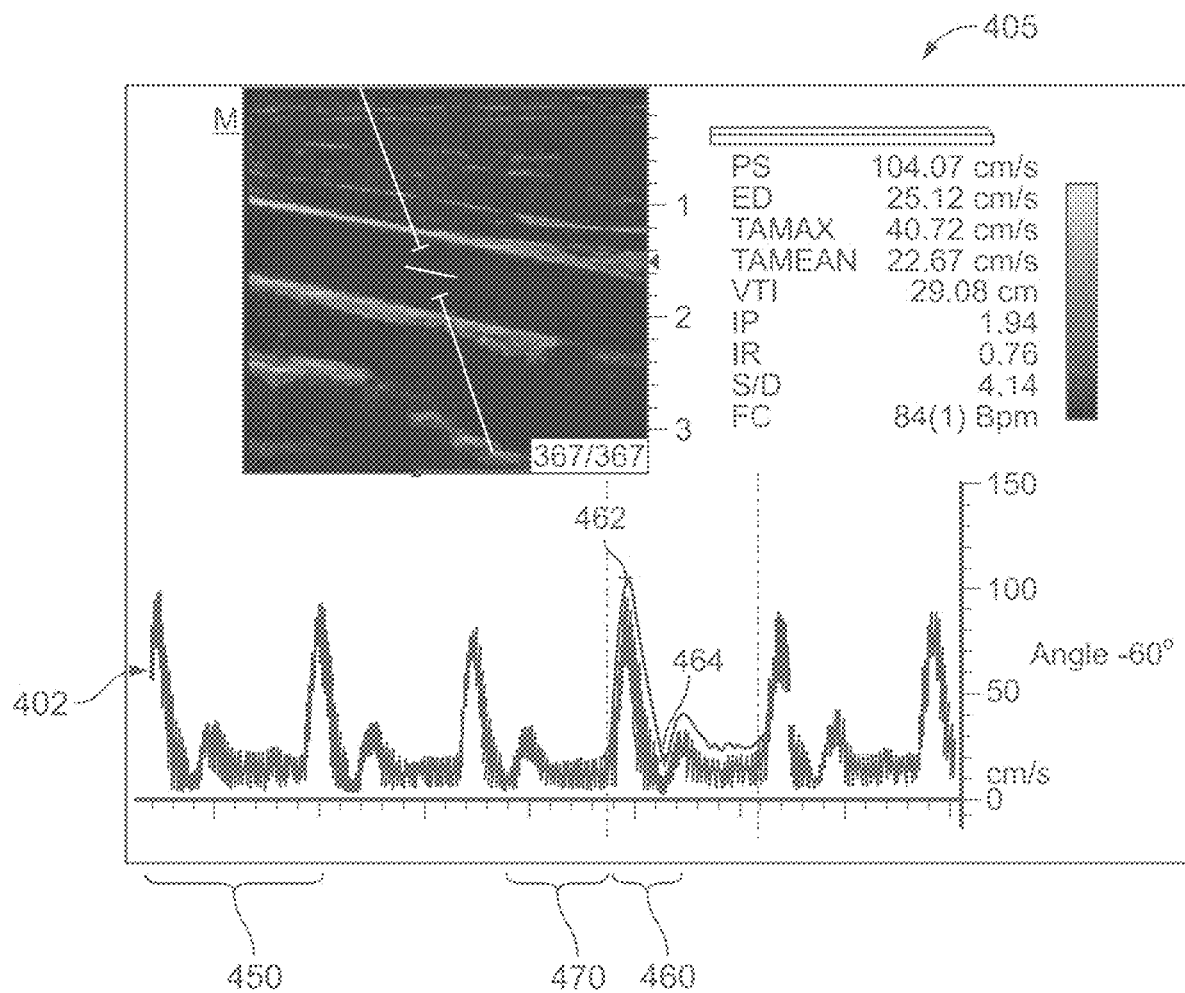
FIG. 9 is a plot of velocity doppler data for a blood pressure monitoring device in accordance with one embodiment of the subject invention.
Figure 10:
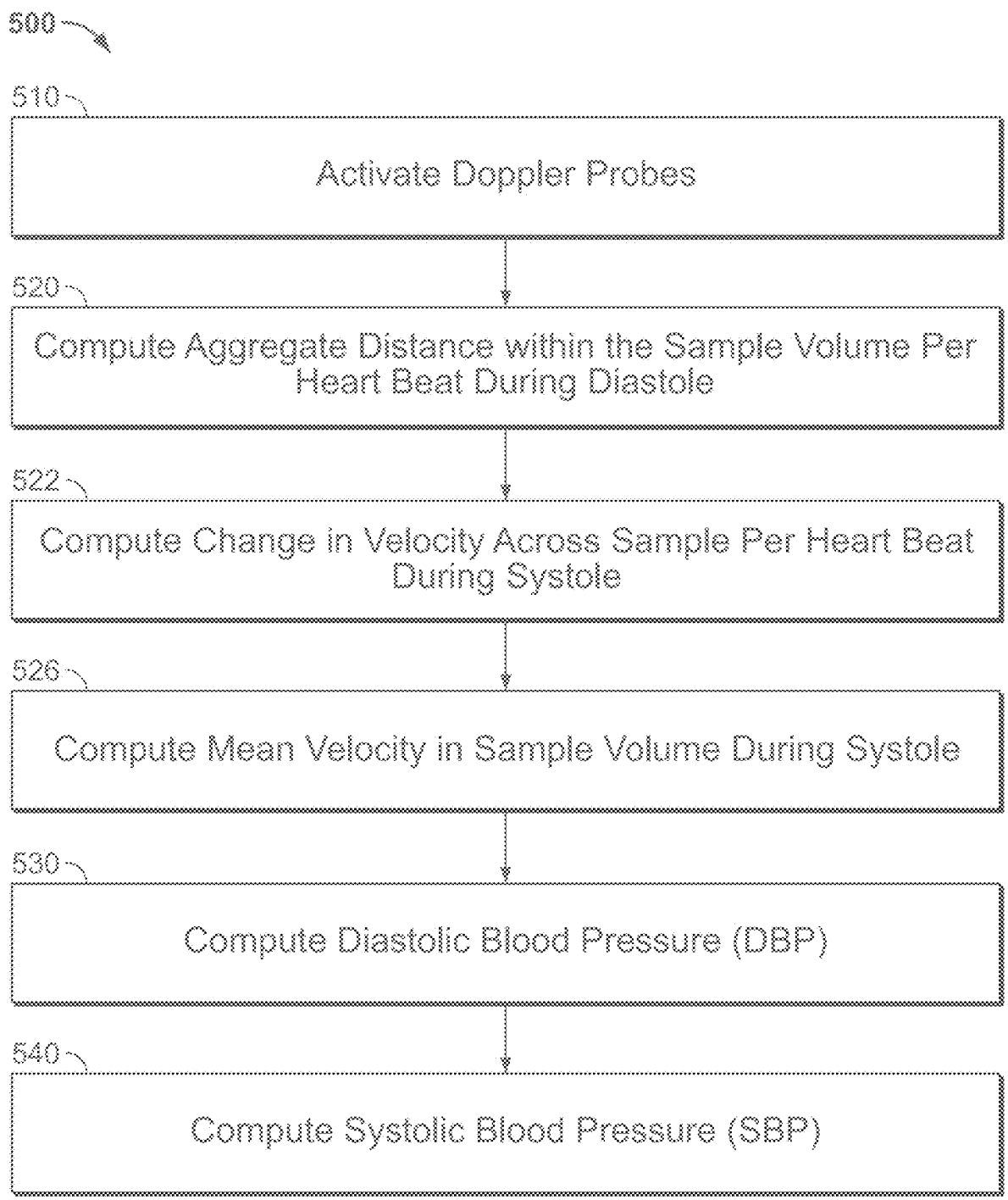
FIG. 10 is a flowchart illustrating a method for computing diastolic and systolic blood pressure in accordance with an embodiment of the invention.

In embodiments of the invention, Applicants define stroke volume (SV) as the volume through a measured artery (during systole) per heart beat ($Vol_a$) multiplied by a relatively constant proportional factor ($P_f$) per patient, or, $$SV = Vol_a \times P_f, \quad [4]$$

where $Vol_a$, also referred to herein cross sectional volume, is the cross sectional area of measured artery (A) multiplied by a "total distance" of the blood travel per heart beat during systole, namely, the area under doppler velocity curve during systole per heart beat ($V_{area}$), discussed further herein in connection with FIG. 9-10, or $$Vol_a = A \times V_{area}. \quad [5]$$

And where the proportional factor $P_f$ may initially may be calculated per user by calibrating the blood pressure monitoring device to a measured blood pressure reading using a conventional means (e.g., an oscillometric compressive cuff device). Alternatively, stroke volume may be directly measured by transthoracic echocardiography and the proportional factor $P_f$ may be subsequently computed based on the measured stroke volume.

Systemic Vascular Resistance (SVR) is the change in pressure (during systole) across an artery (ΔP) divided by volumetric flow (during systole) in an artery ($Vol_f$).

$$SVR = \Delta P / Vol_f, \quad [6]$$

where

ΔP=4ΔVs; and ΔVs is a change in velocity across a measured artery during systole and based on a simplification of Poiseuille's equation.

$Vol_f$ is the cross sectional area of measured artery (A) multiplied by systolic time-average mean velocity in artery ($V_{mean}$), or $$Vol_f = A \times V_{mean}, \quad [7]$$

where $V_{mean}$ is computed by averaging the measured velocities across the vessel.

Based on the above equations, MAP can be simplified as follows:

$$\begin{aligned} MAP &= CO \times SVR \\ &= (HR \times SV) \times SVR \\ &= HR \times (Vol_a \times P_f) \times (4\Delta Vs / Vol_f) \\ &= (HR \times (A \times V_{area}) \times P_f) \times (4\Delta Vs)/(A \times V_{mean}), \text{ therefore} \end{aligned} \quad [8]$$

$$MAP = (HR \times V_{area} \times P_f \times 4\Delta Vs) / V_{mean}$$

Consequently, MAP may be approximated based on the above equation [8] and the values HR, $V_{area}$, ΔVS, and $V_{mean}$ which may be automatically computed from the data received by the doppler probes, discussed herein.

Method for Computing Mean Arterial Pressure

Figure 8:
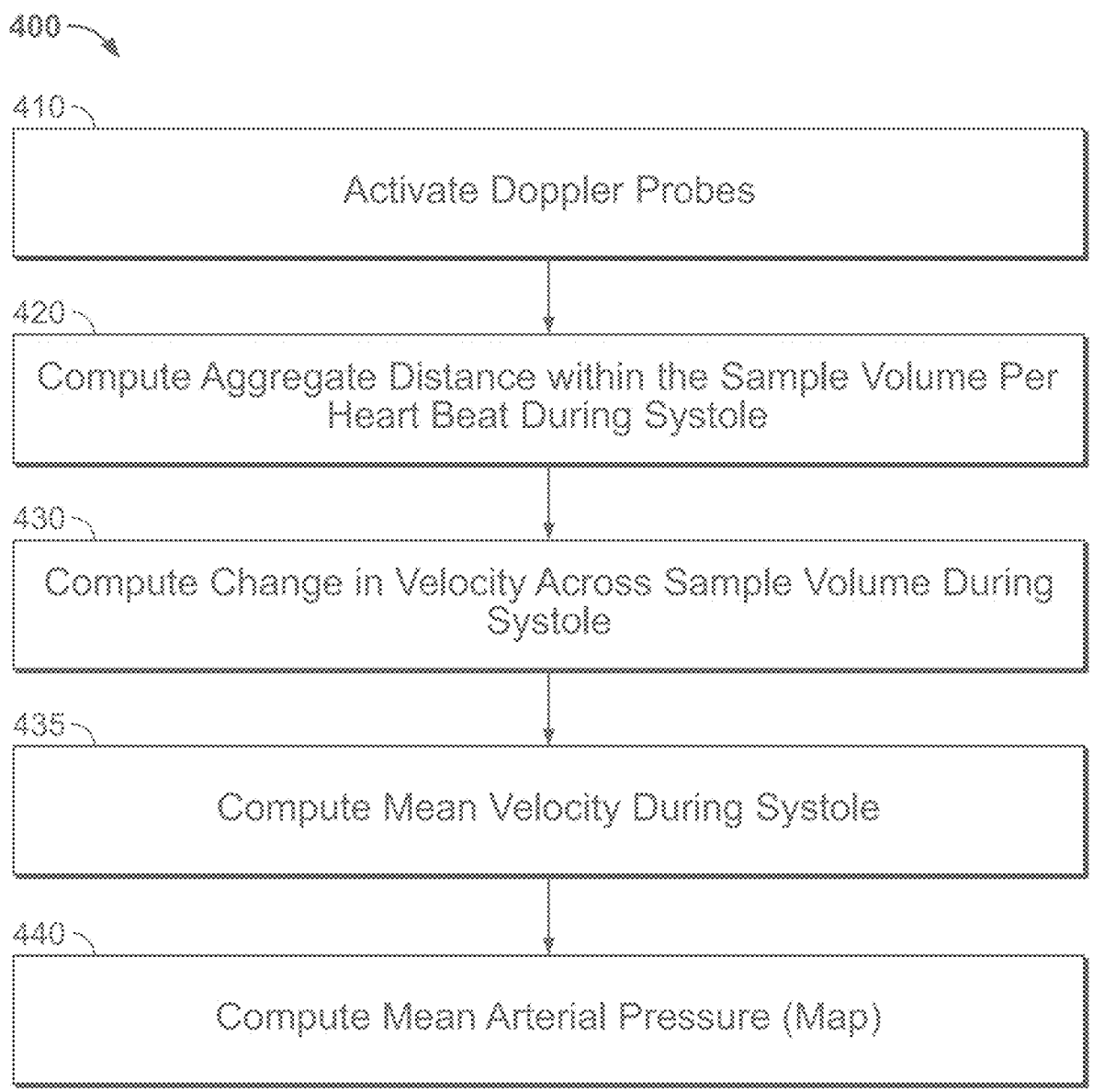
FIG. 8 is a flowchart illustrating a method for computing mean arterial blood pressure in accordance with an embodiment of the invention.

FIG. 8 is a flow chart illustrating a method 400 for computing the mean arterial blood pressure based on the MAP approximation (Equation [8]) described above and the data generated from the doppler probes in accordance with an embodiment of the present invention.

Step 410 states to activate the doppler probes. For example, and with reference to FIGS. 5-6, the doppler probes 110, 112, 114 are activated to capture a live stream of doppler signals. The data is converted from analog to digital by the doppler ultrasound electronics 192 and transmitted to the processor 150 for evaluation as discussed herein.

The doppler probes may be activated by a wide range of techniques. In one embodiment, and with reference again to FIG. 3, the display 140 or button 170 is touched or pushed to activate the doppler probes. In other embodiments, the doppler probes are continuously or periodically activated for continuous monitoring. When activated, in embodiments, the blood pressure monitoring device 100 will stream data to the CPU for a predetermined duration. The duration may range from 1 to 30 seconds, preferably from 5-20 seconds, and more preferably about 8-12 seconds. In one embodiment, the duration is ten (10) seconds.

The volume sampled may vary. In embodiments, the volume sampled ranges from 2 to 10 mm³, and more preferably from 4-8 mm³. In some embodiments, the volume sampled ranges from 2 to 6 mm³, and preferably between 3 and 5 mm³. An example of velocity data 402 from a doppler probe is shown in FIG. 9.

A wide range of waveform features may be determined by evaluating the measured doppler signals 402. For example, heart rate is the time of a complete or full cycle 450. It is listed in the legend 405 of FIG. 9 under the abbreviation "FC." The processor is programmed to automatically compute this value based on the measured doppler waveform 402.

Next, and with reference to step 420, the total/aggregate distance within the sample volume is computed per heart beat during systole, namely, $V_{area}$. An example of $V_{area}$ is shown in FIG. 9 as the value equal to the area under the curve portion 460. The processor is programmed with software to automatically compute this value based on the data received from the doppler probes.

Next, and with reference to step 430, the change in velocity across the measured artery during systole, ΔVs is computed. With reference to FIG. 9, ΔVs is the difference in value between first velocity point (462) and second velocity point (464). The processor is programmed to automatically identify these points and compute the value.

Next, and with reference to step 435, the mean velocity is computed during systole, $V_{mean}$, $V_{mean}$ is computed by averaging the measured velocities across the sample volume during systole. With reference to FIG. 9, e.g., it is shown as the systolic time-averaged mean velocity (TAMEAN) in the legend 405. The processor is programmed to automatically identify this value.

Finally, with reference to step 440, the mean arterial pressure (MAP) is automatically computed by the processor based on the above described computed values and equation [8]:

$$MAP = (HR \times V_{area} \times P_f \times 4\Delta Vs)/V_{mean},$$

where the proportional factor $P_f$ may be determined as described above

Method for Computing Diastolic Blood Pressure

FIG. 10 is a flow chart illustrating a method 500 for computing the diastolic blood pressure (namely, DBP) based on the data streamed from the doppler probes in accordance with an embodiment of the present invention.

Step 510 states to activate the doppler probes. This step may be performed as described above in connection with FIG. 8.

Step 520 states to compute the total/aggregate distance within the sample volume per heart beat during diastole, namely, $W_{Darea}$. An example of $W_{Darea}$ is shown in FIG. 9 as the value equal to the area under curve portion 470. The processor is programmed with software to automatically compute this value based on the data received from the doppler probes.

Next, and with reference to step 522, the change in velocity across the measured artery per heart beat during systole, $\Delta Vs$, is computed. $\Delta Vs$ can be computed as described above in connection with FIG. 8.

Next, and with reference to step 526, the mean velocity is computed during systole, $V_{mean}$. $V_{mean}$ can be computed as described above in connection with FIG. 8.

Next, and with reference to step 530, the diastolic blood pressure (DBP) is automatically computed by the processor according to the following:

$$\begin{aligned}
DBP &= \text{Diastolic Output } (DO) \times SVR \quad [9]\\
&= (HR \times (A \times V_{Darea} \times P_f)) \times (4\Delta Vs/Vol_f)\\
&= (HR \times A \times V_{Darea} \times P_f \times 4\Delta Vs)/(A \times V_{mean}), \text{ therefore}\\
DBP &= (HR \times V_{Darea} \times P_f \times 4\Delta Vs)/V_{mean},
\end{aligned}$$

where HR, $\Delta V$, $P_f$, $P_f$, $V_{mean}$ and $V_{Darea}$ are determined as described above.

Optionally, and with reference to step 540 of FIG. 10, systolic blood pressure (SBP) may be computed on the processor based on the previously computed values DBP and MAP according to the equation [1] set forth above.

Use of Photoacoustics to Determine Map

In another embodiment, photoacoustic information is utilized to determine SVR, and MAP.

Without intending to being bound by theory, in optoacoustic imaging systems, light is used to deliver optical energy to the tissue site, which as a result of optical absorption within the tissue structures (e.g., red blood cells), produce acoustic waves. An image spatially representing the tissue site can be generated by performing image reconstruction on acoustic signals that return to an ultrasound transducer array. In embodiments, blood pressure monitoring apparatuses can include one or more light emitters to direct light towards the artery, serving to generate acoustic waves. Ultrasound probes can be incorporated into the apparatus for receiving or detecting the acoustic signals arising from the light. Examples of photoacoustic devices and techniques for imaging tissue are described in, e.g., US Patent Publication No. 20190150749A1, filed Nov. 21, 2018, and entitled "OPTOACOUSTIC PROBE" and Wang et al., "Ultrasound-mediated biophotonic imaging: A review of acousto-optical tomography and photo-acoustic tomography", Disease Markers 19 (2003, 2004) 123-138.

As described above, SVR is initially computed in order to determine MAP. SVR is defined as follows:

$$\begin{aligned}
SVR &= \Delta P/Vol_f, \text{ where } \Delta P = (8 \times \mu \times L \times Vol_f)/(\pi \times r^4)\\
&\Rightarrow SVR = [(8 \times \mu \times L)/(\pi \times r^4)]/Vol_f\\
&\Rightarrow SVR = (8 \times \mu \times L)/(\pi \times r^4)
\end{aligned}$$

$\Rightarrow SVR=(8 \times \mu \times L)/(\pi \times r^4)$ where $\mu$=viscosity of blood (optionally measured directly by photoacoustics); L=length of artery (optionally measured based on the length of probe used); and r=radius of artery (optionally measured directly measured by photoacoustics).

Next, MAP is computed.

$$\begin{aligned}
MAP &= CO \times SVR, \text{ where Cardiac Output } (CO) = HR \times SV\\
&= (HR \times SV) \times SVR\\
&= HR \times (Vol_a \times P_f) \times (8 \times \mu \times L)/(\pi \times r^4)\\
&= (HR \times (\pi \times r^2 \times V_{area}) \times P_f) \times (8 \times \mu \times L)/(\pi \times r^4)\\
MAP &= (HR \times V_{area} \times P_f \times 8 \times \mu \times L)/r^2,
\end{aligned}$$

where heart rate (HR) may be measured by doppler or optionally photoacoustics, and $P_f$ may be calculated as described above.

Next, the diastolic blood pressure (DBP) can be automatically computed by the processor according to the following:

$$\begin{aligned}
DBP &= \text{Diastolic Output } (DO) \times SVR\\
&= (HR \times (Vol_D \times P_f)) \times ((8 \times \mu \times L)/(\pi \times r^4)),\\
&= (HR \times (\pi \times r^2 \times V_{Darea}) \times P_f) \times ((8 \times \mu \times L)/(\pi \times r^4))\\
&= (HR \times V_{Darea} \times P_f \times 8 \times \mu \times L)/r^2,
\end{aligned}$$

where HR, $P_f$, L, r, $\mu$, and $V_{Darea}$ are determined as described above.

Finally, systolic blood pressure (SBP) may be computed based on equation [1] set forth above, or $$SBP = (3 \times MAP) - (2 \times DBP),$$

where MAP and DBP are the values computed as described above.

Computational Model

Although one exemplary model was described above for automatically computing MAP based on the doppler velocity data, a wide variety of models may be used to compute the blood pressure from the features extracted from the doppler waveforms. In embodiments, a machine learning or AI model is employed to estimate the blood pressures (MAP, DBP, SBP) based on the features described above. Examples of suitable models include artificial neural networks (e.g., CNN). In embodiments, a CNN is trained on user data to correlate the various extracted features (such as the extracted features described above) to the blood pressures.

Function approximation using machine learning (e.g., deep neural nets) is described in various publications such as, for example, Jonas Adler et al, "Solving ill-posed inverse problems using iterative deep neural networks", Inverse Problems, Volume 33, Issue 12, (2017). The function approximation model can be trained on data gathered through simultaneously value recording using the novel blood pressure monitoring device described herein and a sphygmomanometer on a diverse group of subjects. The above described extracted features are correlated with the actual measured BP values. The trained model would not require calibration for each user.

Alternative Embodiments

Although the apparatus is described as arranged on the wrist, it could be configured otherwise. The device could be configured to read blood velocity data from another part of the body where there is an artery that is close to the surface of the skin. Examples of other configurations include, without limitation, handheld probes, rings, and belts whether surrounding the chest, waist, thigh or another area.

Figure 11:
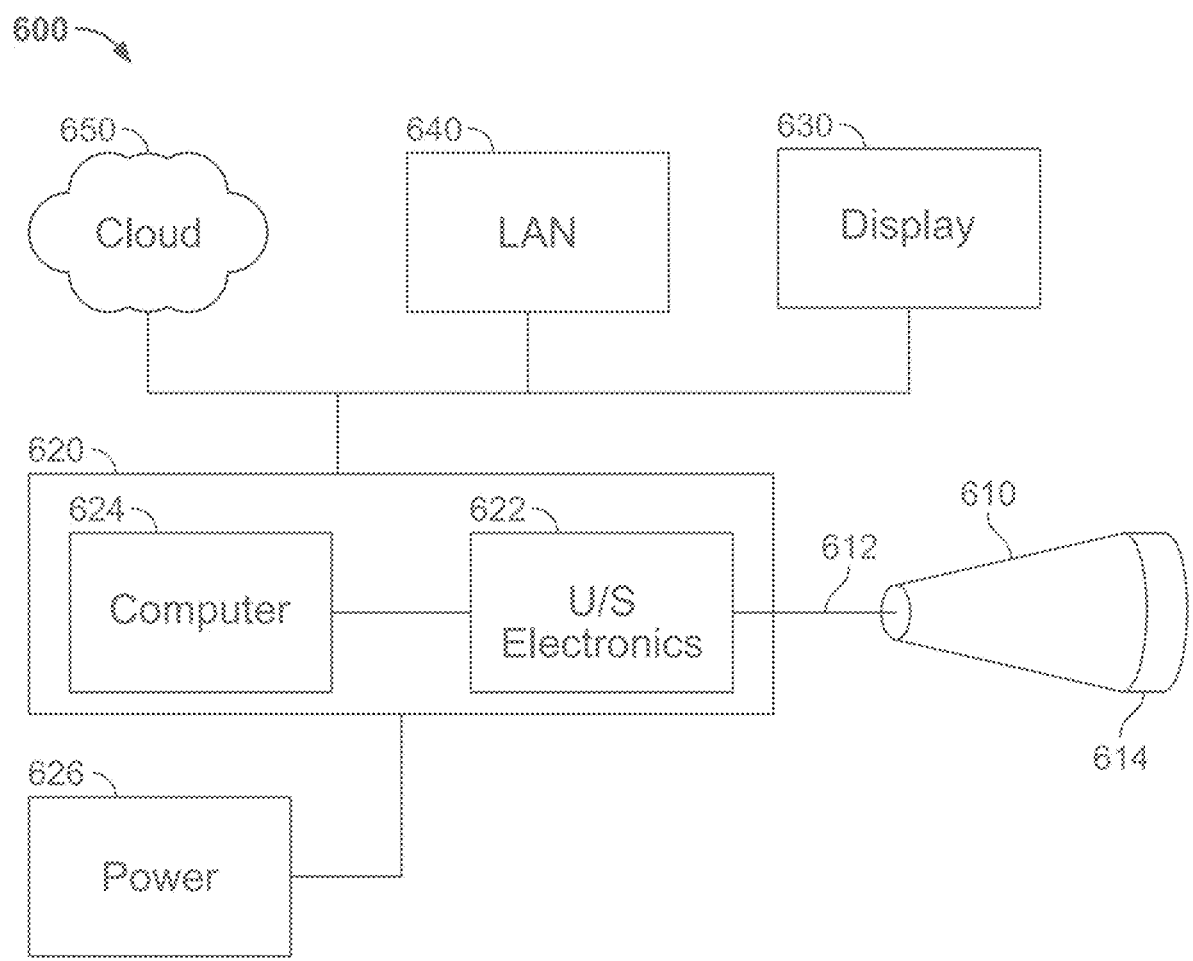
FIG. 11 is a schematic illustration of another blood pressure monitoring system in accordance with an embodiment of the invention.

With reference to FIG. 11, a blood pressure monitoring system 600 in accordance with another embodiment of the invention includes a handheld probe 610 coupled to a console 620 by an umbilical cord 612. The handheld probe can have doppler arranged within its head 614 as described above so as to project sound waves to and from the head surface. Optionally, light is delivered into the tissue through an acoustically (and optionally light) transparent window in head 614 to produce acoustic signals arising from optical absorption of the light by the tissue (e.g., red blood cells). The console 620 can enclose ultrasound electronics 622 and a central computer 624 programmed and operable as described above. Power 626 can be supplied to the system from a hospital power source such as 120V/110AC or electric outlet. A display 630, optionally, touchscreen display, is shown for communicating information with users.

Additionally, data, program updates, and other communications can be sent to and from a local area network 640 or a remote server or cloud 650.

The blood pressure monitoring system 600 has some advantages over the smaller wearables described above because the console 620 has a larger footprint for housing electronics and power. Thus, in some instances where it is not necessary to wear the BP device continuously, the non-invasive non-compressive blood pressure monitoring system 600 can be applied in an outpatient or inpatient type environment to determine blood pressure using the algorithms described herein.

It is also to be understood that in embodiments the device may be operable to communicate information and to be controlled by a remote device such as a tablet, smart phone or laptop as well as send data to a remote processor (e.g., cloud based).

Additionally, in other embodiments, additional types of sensors are combined or substituted for one or more of the doppler sensors. For example, with reference to FIG. 2, one or more of the individual doppler probes of pairs 110, 112 may be replaced with a light emitter and detector. Preferably, the sensors are self-contained/stand-alone and include their own processing electronics to provide a signal to the CPU. However, in embodiments, less sophisticated emitters and detectors and cameras may be incorporated into the apparatus and the raw data sent to the processor for pre-processing and evaluation.

In embodiments the apparatus includes a plurality of modes of operation including without limitation a location mode, calibration mode, and/or monitoring mode.

In embodiments, the vessel location mode or module is operable to alert the user to an optimal position on the skin to hold the apparatus. This location mode (versus the above described blood pressure monitoring modes) may be activated by the user to commence energy delivery into the skin. In the location mode the energy emitters transmit energy into the skin and the doppler electronics send the processed data to the main processor for evaluation. In embodiments, the processor is operable during the location mode to alert the user (e.g., via sound, vibration, or visual indicator) to the optimal position as the user moves the apparatus (whether a wearable or handheld device) along the skin. The user can scroll back and forth along a skin area to search for an optimal position. The audio indicator may be operable to increase in volume or pitch as the measured blood velocity (e.g., TAMAX, described above) increases. Similarly, the device can be operable to provide visual feedback (e.g., light color or brightness) or tactile feedback (e.g., vibration generated by a small electromechanical actuator or motor) corresponding to a change in velocity with position along the skin. Once the user is satisfied with the position, the user straps or holds the device in place and activates the blood pressure monitoring mode.

In embodiments, the calibration mode prompts the user for a blood pressure reading (or another blood pressure-related parameter such as stroke volume) taken by alternative means (e.g., an oscillometric compressive cuff device, catheter, etc.). The proportionality factor of the user is automatically computed by the apparatus by equating a reading as measured by the apparatus itself (e.g., apparatus 100, 610, and assuming a placeholder/estimate value for $P_f$), and the actual reading as measured by the alternative device (e.g., an oscillometric compressive cuff) and solving the equations described herein for the proportionality factor $P_f$. In preferred embodiments, the calibration mode prompts the user to repeat calibration several times until the proportionality factor is constant.

In embodiments, the monitoring mode can be performed subsequent to the location and calibration mode as described above and, for example, with reference to FIGS. 8 and 10.

Although a number of embodiments have been disclosed above, it is to be understood that other modifications and variations can be made to the disclosed embodiments without departing from the subject invention. Indeed, any of the components described herein may be combined with one another except where such components are exclusive to one another. Any of the steps described herein may be combined in any combination and sequence except where such steps are exclusive to one another.

The invention claimed is:

1. A blood pressure monitoring device for computing mean arterial pressure (MAP) of a user comprising:
   a case and a strap adapted to hold the case against a wrist of the user;
   at least one doppler probe arranged within the case and aimed at a first location of an artery in the wrist when the case is strapped to the wrist; and a memory arranged with the case and a MAP equation stored thereon;

a processor arranged within the case and programmed and operable to:

compute a plurality of features from velocity data generated by the at least one doppler probe corresponding to the first location of the artery; and solve the MAP equation to compute the MAP based on the plurality of features corresponding to the first location of the artery and without data corresponding to elevational changes in the first location.

2. The blood pressure monitoring device of claim 1, wherein the MAP equation is defined as follows:

$MAP=(HR \times V_{area} \times P_f \times 4\Delta Vs)/V_{mean}$, wherein HR is heart rate, $V_{area}$ is the cross sectional area of the measured artery multiplied by a total distance of blood travel per heart beat during diastole, $\Delta Vs$ is the change in velocity across the measured artery during systole, $V_{mean}$ is the mean velocity during systole, and $P_f$ is a proportionality factor calculated per user by calibrating the blood pressure monitoring device to a measured blood pressure reading using a conventional BP measurement device.

3. A method for monitoring mean arterial pressure (MAP) of a user comprising:

activating at least one doppler probe aimed at a first location of an artery in a wrist of the user to generate doppler velocity data corresponding to the first location of the artery; and automatically computing on a processor:

a plurality of features from the doppler velocity data corresponding to the first location of the artery; and solving a MAP equation to calculate the MAP of the user based on the plurality of features corresponding to the first location of the artery and without data corresponding to elevational changes in the first location.

4. The method of claim 3, wherein one of the plurality of features comprises: a change in velocity across the artery during systole.

5. The method of claim 4, wherein the plurality of features comprises $V_{area}$, where $V_{area}$ is a cross sectional area of the measured artery multiplied by a total distance of blood travel per heart beat during the systole, and a time-averaged mean velocity during the systole.

6. The method of claim 3, further comprising directing light into the artery.

7. The method of claim 6, wherein the doppler velocity data is based, at least in part, on absorption of the light by the artery and blood flow therethrough.

8. The method of claim 3, further comprising alerting the user to an optimal position on the wrist to strap the case thereto as the user adjusts and moves the case along the user's wrist.

9. The method of claim 7, wherein the MAP equation is defined as follows:

$MAP=(HR \times V_{area} \times P_f \times 8 \times \mu \times L)/r^2$, wherein

HR is heart rate, L is length of the artery measured, $V_{area}$ is the cross sectional of the measured artery multiplied by a total distance (L) of blood travel per heart beat during diastole, $\mu$ is viscosity of blood, and r is radius of the artery, and $P_f$ is a proportionality factor calculated per user by calibrating the blood pressure monitoring device to a measured blood pressure reading using a conventional BP measurement device.

10. A blood pressure monitoring system for computing mean arterial pressure (MAP) of a user comprising:

a case and a window adapted to be held against a skin of the user;

at least one doppler probe arranged within the case; and a processor programmed and operable to:

compute a plurality of features from velocity data arising from at least one of the at least one the doppler probe corresponding to a first location of an artery; and solving a MAP equation to compute the MAP based on the plurality of features corresponding to the first location of the artery and without data corresponding to elevational changes in the first location.

11. The blood pressure monitoring system of claim 10, wherein the case further comprises a light emitter to direct light through the window towards the artery.

12. The blood pressure monitoring system of claim 11, wherein the doppler velocity data is based, at least in part, on absorption of the light by the artery and blood flow therethrough.

13. The blood pressure monitoring system of claim 12, wherein the plurality of features comprise viscosity, heart rate, and radius of the artery.

14. The blood pressure monitoring system of claim 10, wherein the processor is further operable to compute systolic blood pressure (SBP) based on the velocity data, and optionally, to compute diastolic blood pressure based on the computed MAP and SBP.

15. The blood pressure monitoring system of claim 10, further comprising a console, and the processor is enclosed within the console.

16. The blood pressure monitoring system of claim 15, wherein the case, window, light emitter, and at least one doppler probe are incorporated together as a handheld tool connected to the console by an umbilical cord.

17. The blood pressure monitoring system of claim 10, wherein the at least one doppler probe comprises a plurality of doppler probes, and wherein at least one of the plurality of doppler probes sends acoustic waves towards the artery and at least one of the plurality of doppler probes receives acoustic waves from the artery.

18. The blood pressure monitoring system of claim 10, further comprising a location module for alerting the user to an optimal position on the skin to press the window thereto as the user moves the window along the user's skin.

19. The blood pressure monitoring system of claim 10, wherein the mean arterial pressure (MAP) is based on a patient-specific proportionality factor, and the system further comprises a calibration module operable to prompt the user for an actual blood pressure-related reading, and to compute the patient-specific proportionality factor based on the actual blood pressure-related reading.

20. The blood pressure monitoring system of claim 10, further comprising a display, and wherein the strap, case and display collectively form a wrist watch-like shape.

21. The blood pressure monitoring system of claim 10, wherein the MAP equation is defined as follows:

$MAP=(HR \times V_{area} \times P_f \times 4\Delta Vs)/V_{mean}$, wherein HR is heart rate, $V_{area}$ is the cross sectional area of the measured artery multiplied by a total distance of blood travel per heart beat during diastole, $\Delta Vs$ is the change in velocity across the measured artery during systole, $V_{mean}$ is the mean velocity during systole, and $P_f$ is a proportionality factor calculated per user by calibrating the blood pressure monitoring device to a measured blood pressure reading using a conventional BP measurement device.

* * * * *